United States Patent
Koschmieder et al.

(10) Patent No.: US 8,066,374 B2
(45) Date of Patent: Nov. 29, 2011

(54) OPTICAL SYSTEM FOR A FUNDUS CAMERA

(75) Inventors: Ingo Koschmieder, Jena (DE); Manfred Dick, Gefell (DE); Detlef Biernat, Jena (DE); Jan Buchheister, Jena (DE); Lothar Mueller, Ottendorf (DE)

(73) Assignee: Carl Zeiss Meditec, AG, Jena (DE)

( * ) Notice: Subject to any disclaimer, the term of this patent is extended or adjusted under 35 U.S.C. 154(b) by 67 days.

(21) Appl. No.: 12/520,010

(22) PCT Filed: Dec. 18, 2007

(86) PCT No.: PCT/EP2007/011089
§ 371 (c)(1),
(2), (4) Date: Jul. 14, 2009

(87) PCT Pub. No.: WO2008/077526
PCT Pub. Date: Jul. 3, 2008

(65) Prior Publication Data
US 2010/0014052 A1  Jan. 21, 2010

(30) Foreign Application Priority Data
Dec. 21, 2006 (DE) .................. 10 2006 061 933

(51) Int. Cl.
*A61B 3/14* (2006.01)
*A61B 3/10* (2006.01)
(52) U.S. Cl. ............. 351/207; 351/206; 351/220
(58) Field of Classification Search .......... 351/206, 351/207, 220
See application file for complete search history.

(56) References Cited

U.S. PATENT DOCUMENTS

| | | | |
|---|---|---|---|
| 4,730,910 A | 3/1988 | Humphrey | |
| 4,838,680 A | 6/1989 | Nunkawa | |
| 5,198,845 A | 3/1993 | Triller | |
| 6,585,374 B2 | 7/2003 | Matsumoto | |
| 6,736,507 B2 | 5/2004 | Kudryashov et al. | |
| 7,500,753 B2 | 3/2009 | Mueller et al. | |
| 2001/0022689 A1* | 9/2001 | Takeyama | 359/625 |
| 2005/0030474 A1 | 2/2005 | Sumiya | |
| 2006/0215111 A1* | 9/2006 | Mihashi | 351/205 |
| 2006/0232853 A1 | 10/2006 | Dobschal et al. | |
| 2007/0047070 A1* | 3/2007 | Sander | 359/368 |

FOREIGN PATENT DOCUMENTS
DE  479 622  6/1929
(Continued)

*Primary Examiner* — Jordan Schwartz
(74) *Attorney, Agent, or Firm* — Frommer Lawrence & Haug LLP

(57) ABSTRACT

The invention is directed to an optical system for a fundus camera for reflection-free opthalmoscopy having a beam path with refractive and reflective optical elements which are used substantially in common for illumination and observation or recording. An imaging mirror system substantially comprising a plurality of reflecting optical elements in the form of mirrors and is provided for illuminating and imaging the fundus. At least one optical element, for example, mirror, is formed as a freeform mirror with an imaging, reflecting freeform surface. The optical elements are arranged in a housing in a precisely defined position and attitude relative to one another in such a way that an imaging of the reflecting surfaces of the optical elements on the image of the imaged retina is prevented within a wide diopter range of the patient's eye to be examined.

20 Claims, 2 Drawing Sheets

FOREIGN PATENT DOCUMENTS

| | | |
|---|---|---|
| DE | 524 378 | 4/1931 |
| DE | 35 19 442 | 12/1985 |
| DE | 38 21 973 | 2/1990 |
| DE | 103 16 416 | 10/2004 |
| DE | 10 2005 017 207 | 10/2006 |
| EP | 0 980 680 | 2/2000 |
| EP | 1 319 362 | 6/2003 |
| EP | 1 609 405 | 12/2005 |
| WO | WO 98/27863 | 7/1998 |
| WO | WO 2004/086962 | * 10/2004 |

* cited by examiner

OPTICAL SYSTEM FOR A FUNDUS CAMERA

The present application claims priority from PCT Patent Application No. PCT/EP2007/0011089 filed on Dec. 18, 1007, which claims priority from German Patent Application No. DE 10 2006 061 933.1 filed on Dec. 21, 2006, the disclosure of which is incorporated herein by reference in its entirety.

BACKGROUND OF THE INVENTION

1. Field of the Invention

The invention is directed to an optical system for a fundus camera used for the observation and imaging of the ocular fundus. When the ocular fundus is imaged with a camera of this kind, there are generally reflections at the cornea and at surfaces of the imaging optical system which have a negative effect on the quality of the images and the evaluation thereof.

2. Description of Related Art

A fundus camera basically comprises a multi-stage optical system in which an opthalmoscope lens generates an intermediate image that is imaged by a tracking system or main objective onto a film, onto a CCD matrix of a CCD camera, or also in an intermediate image for visual observation with an ocular. In this system, the opthalmoscope lens is also a component part of the elements of the illumination system.

Reflections at the cornea and at the surfaces of the opthalmoscope lens pose a special problem in the observation and recording of the fundus because the light which is reflected by the retina and which carries the information of actual interest has a substantially lower intensity than the light which is reflected before entering the eye. Interfering cornea reflections are usually prevented by partitioning the pupil of the eye. For this purpose, the opthalmoscope lens images an illumination ring in the eye pupil. The illumination beams reflected at the cornea miss the aperture of the observation system. Only the area inside the illumination ring is used for observation.

DE-OS 35 19 442 describes an optical system in which light components which could enter the observation aperture through reflection at the opthalmoscope lens or at the cornea are blocked out by means of "black point plates" which are arranged at a suitable location in the beam path and which are coated in a defined manner by light-absorbing layers. This type of reflection suppression has come to be known as "anti-reflection point." A disadvantage of this concept is the proximity of the anti-reflection point to the field diaphragm. The absorption of the individual light components can become visible as irregular illumination of the fundus. Ring-shaped shadows occur which impair the image impression and, therefore, impede evaluation by the doctor.

DE 103 16 416 describes an optical system in which a multilens objective is provided in place of the opthalmoscope lens. The lenses of the multilens objective are tilted relative to one another in such a way that direct reflections at the interfaces do not enter the aperture of the observation system. Tilting in the x-direction and y-direction is provided for each pair of lenses. This optical system requires a substantial outlay for mechanical mounts for the individual lenses of the objective. Further, transverse chromatic aberrations and longitudinal chromatic aberrations are produced and must be compensated at great expense in the downstream optics system, both in the observation portion of the beam path and in the illumination portion of the beam path. In applications with very small beam diameters, e.g., in laser applications, the large quantity of optical interfaces and the long glass path within the objective are also disadvantageous. Even slight contamination at the interfaces and in the material of the optical components that are used can adversely mount up, sharply reduce the intensity of the light and generate interfering scattered light.

An arrangement with tilted lenses is also described in U.S. Pat. No. 4,730,910.

Further, fundus cameras are known which have mirror elements in place of the opthalmoscope lens. These systems have simple mirror geometries with which only a small observation field and illumination field can be implemented with adequate optical quality.

Other mirror systems such as those described, e.g., in U.S. Pat. No. 6,585,374, use moving elements to expand the small observation field and illumination field based on scanning principles. However, such systems need complicated mechanisms for precise movement of the elements in question and require complicated image processing techniques.

SUMMARY OF THE INVENTION

Therefore, it is the object of the invention to provide an optical system for a fundus camera in which an imaging of the fundus with a large observation field and a large working distance is achieved without interfering reflections and substantially without chromatic aberrations through the use of a few, primarily reflecting, optical elements for imaging.

In an optical system designed according to the features of the preamble of the first patent claim, the above-stated object is met according to the invention through the features indicated in the characterizing part of this claim. Advantageous embodiments and details of the optical system according to the invention are disclosed in the dependent claims.

Imaging fidelity across an illumination field and observation field appreciably greater than 30° is made possible in that at least one mirror is constructed as a freeform surface.

An advantageous system for implementing an opthalmoscopy which is substantially free from reflections is achieved by providing a mirror system comprising two freeform mirrors which are constructed as symmetry-free freeform mirrors, between which the intermediate image is located in space at a suitable location. In this construction of both mirrors as curved freeform surfaces, a distribution of the refractive powers having an advantageous effect on imaging errors and small deflection angles are realized. A particularly advantageous compensation of asymmetric imaging errors is realized through the use of symmetry-free freeform surfaces.

In order to achieve optical systems with very low scattered light, it is advantageous that the mirror system is arranged so as to be encapsulated in a housing which is closed by a cover plate, respectively, at the side facing the patient and at the side facing the observer. The cover plates themselves are designed in such a way with respect to their surface shape that any interfering reflections which may occur cannot enter the observation apparatus, and chromatic aberrations are kept at a minimum. In this way, scattering of light which is caused especially by dust or other impurities on the reflecting surfaces and which adversely affects imaging of the fundus is efficiently minimized.

In order primarily to simplify the mounting and alignment of the mirrors, it is advantageous when the optical elements of the mirror system are arranged in the housing in a common holder or receptacle in a precisely defined position and attitude relative to one another. This holder is designed in such a way that the mirrors have a fixed reference in relation to the holder and to one another which allows the mirrors to be positioned with the required accuracy in one mounting step without alignment in the housing.

It is also advantageous when the mirror system comprises a monolithic body of optical material with an index of refraction n>1 at which the imaging reflective surfaces are provided at precisely defined positions in a precisely predetermined surface shape, and a light entry surface and light exit surface are provided. Since they are refractive surfaces in this case, the light entry surface and the light exit surface are provided with a surface shape such that interfering reflections are prevented and chromatic aberrations are minimized. The monolithic construction obviates time-consuming alignment of the reflecting surfaces of the mirrors so that this system is very easy to assemble.

Further, it can be advantageous that the light entry surface and/or light exit surface of the monolithic body are/is shaped asymmetrically.

In order to compensate for device-specific errors and/or higher-order visual acuity deficiencies and to obtain optimally corrected fundus images, it is advantageous to provide at least one reflecting, electronically structurable or adaptive optical element. It is advantageous to arrange the adaptive elements in the vicinity of the device pupil.

Further, it can be advantageous when at least one of the optical elements of the mirror system is constructed as a spectral color splitter.

An advantageously designed embodiment form of an optical system according to the invention is provided, for example, when the position of the mirrors 1 and 2 which are constructed as freeform mirrors have the following coordinates corresponding to:

a translation of the coordinate system with respect to the eye pupil (in air) of:

| Coordinate | X [mm] | Y [mm] | Z [mm] |
|---|---|---|---|
| Eye pupil | 0.0000000 | 0.0000000 | 0.0000000 |
| Mirror 1 | −6.8487090 | −165.4836370 | 47.0325630 |
| Mirror 2 | 293.0630880 | −0.6361000 | −155.3942110 |
| Image of the illumination ring | 40.6840860 | 107.9439940 | 84.9774900; | a rotation of the coordinate system with respect to the eye pupil (in air) of:

| Angle of rotation | α [°] | β [°] | γ [°] |
|---|---|---|---|
| Eye pupil | 0.0000000 | 0.0000000 | 0.0000000 |
| Mirror 1 | 76.0042720 | −1.9900470 | 0.0000000 |
| Mirror 2 | 170.9745940 | −64.6866110 | 0.0000000 |
| Image of the illumination ring | −51.2908710 | 39.1319540 | 30.6900040; | and a surface shape for mirrors 1 and 2 with respect to the respective surface coordinate system, which surface shape is defined by the following equation:

$$z = (p_x x^2 + p_y y^2)/[1 + \sqrt{1-(1+k_y)p_x^2 x^2 - (1+k_y)p_y^2 y^2}] + c_1 x + c_2 y + c_3 x^2 + c_4 xy + c_5 y^2 + c_6 x^3 + c_7 x^2 y + c_8 xy^2 + c_9 y^3 + c_{10} x^4 + c_{11} x^3 y + \ldots;$$

where a polynomial development with the development constants $c_{1-27}$ has the following values for mirror 1:

| | $K_x = 0.000000000E+00$ | | $K_y = 0.000000000E+00$ | |
|---|---|---|---|---|
| | $1/\rho_x = -215.000$ | | $1/\rho_y = -219.000$ | |
| $c_{1-4}$ | 0.00000000E+00 | 0.00000000E+00 | −.11000521E−03 | −.14259467E−03 |
| $c_{5-8}$ | 0.36710319E−04 | 0.30325236E−06 | 0.39598788E−06 | .72428906E−06 |
| $c_{9-12}$ | −.22614328E−06 | 0.56301184E−08 | 0.18564567E−08 | −.17641549E−08 |
| $c_{13-16}$ | 0.300856709E−08 | −.11779725E−08 | −.16133079E−10 | −.29826733E−10 |
| $c_{17-20}$ | −.10722833E−11 | 0.47271735E−12 | −.20450551E−10 | .55932153E−11 |
| $c_{21-24}$ | −.15323720E−13 | 0.14840899E−12 | −.48945914E−13 | 0.22616480E−13 |
| $c_{25-27}$ | 0.15323720E−13 | 0.12953501E−13 | −.87761187E−15; | | where a polynomial development with the development constants $c_{1-27}$ has the following values for mirror 2:

| | $K_x = 0.000000000E+00$ | | $K_y = 0.000000000E+00$ | |
|---|---|---|---|---|
| | $1/\rho_x = 0.000$ | | $1/\rho_y = 137.000$ | |
| $c_{1-4}$ | 0.00000000E+00 | 0.00000000E+00 | 0.43292571E−03 | −.14593775E−03 |
| $c_{5-8}$ | −.42509202E−02 | −.28647132E−07 | 0.45437799E−06 | −.11927701E−05 |
| $c_{9-12}$ | 0.22797954E−05 | 0.39691471E−09 | 0.48994174E−09 | 0.22211437E−08 |
| $c_{13-16}$ | −.12740305E−08 | −.92954442E−08 | −.29905067E−12 | −.27840314E−11 |
| $c_{17-20}$ | −.42513819E−13 | −.56277965E−11 | −.45816012E−10 | −.24706205E−09 |
| $c_{21-24}$ | −.55720016E−15 | 0.18029456E−14 | −.34158468E−14 | −.48883050E−14 |
| $c_{25-27}$ | 0.33724484E−13 | 0.51120041E−12 | −.27001064E−11; | | and where $\rho_x$ and $\rho_y$ are curvatures in the origin of the respective surface coordinate systems, $K_x$ and $K_y$ are conical constants, and x; y; z are the coordinates of the surface points of the mirrors.

For fluorescence applications, it can be advantageous when one of the mirrors is constructed as a spectral color splitter. In this way, the excitation light in fluorescence applications can be introduced very close to the application point. This substantially simplifies the construction of the entire optical system of the device because color splitters and other additional components for correcting the expanded spectral bandwidth are not necessary.

It can also be advantageous to provide means for generating sequential light pulses in different spectral regions, means for synchronized image acquisition by means of an image sensor, and means for image processing for displaying and storing a color image or any other combinations or monochrome individual images.

Further, it is advantageous when one or more adjustable optical elements which change their position synchronously with light pulses are provided for selective compensation of chromatic aberrations.

Further, means for selective compensation of chromatic aberrations in the form of optical elements of at least one adaptive optical component which are adjusted synchronously with light pulses can be provided in an advantageous manner.

The optical system for reflection-free opthalmoscopy can be applied in an advantageous manner in devices for multicolor laser coagulation, for carrying out optical coherence tomography (OCT), and in devices for the diagnosis and therapy of the eye by ultrashort pulse lasers.

Application in hyperspectral imaging or in multispectral imaging for diagnosing retinal functions in fundus reflectometry is advantageous.

Application in fundus cameras based on a traditional generation of color images parallel in time or based on a new generation of color images sequentially in time, or based on a sequential multispectral fundus reflectometry with a monochrome chip is also advantageous.

The use of the freeform mirror optics in devices with OCT, confocal or line laser scanners or in device and/or methods for imaging the retina can also be advantageous.

Further, application in confocal laser scanners is advantageous.

Further, application of the freeform mirror optics in opthalmological devices, particularly fundus cameras, with LEDs operating in continuous operation and/or in pulsed operation as illumination source is advantageous. Aside from eliminating reflections in the recordings, a suppression of motion blur can be successfully carried out because of the short exposure times which can be achieved by the LEDs.

In particular, by minimizing the distance between the patient's eye being examined and the mirror next to the patient, the overall dimensions of the optical system can also be minimized.

When using an optical imaging system comprising mirrors, no unwanted reflections occur at optical interfaces. Accordingly, there is no longer any need to block out portions of light in the illumination optics. Unwanted ring-shaped shadows on the image of the retina do not occur. The absence of chromatic aberrations in the mirror system makes it possible to simplify the optical system. In this system, the intermediate image can be positioned in such a way that no optical surfaces are imaged on the retina image in the range within which most visual acuity deficiencies occur. Owing to the additional degrees of freedom made possible by the freeform mirrors which are used, the imaging fidelity is ensured over an illumination field and over an observation field of >30°. In the optical system according to the invention, all of the components are arranged in such a way that there is a free working distance of about 30 mm to 50 mm between the eye of the patient and a component so that ergonomic concerns relating to the patient are taken into account and the doctor has sufficient room to maneuver.

In particular, the overall dimensions of the optical system can also be minimized by minimizing the distance between the patient's eye being examined and the mirror next to the patient.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
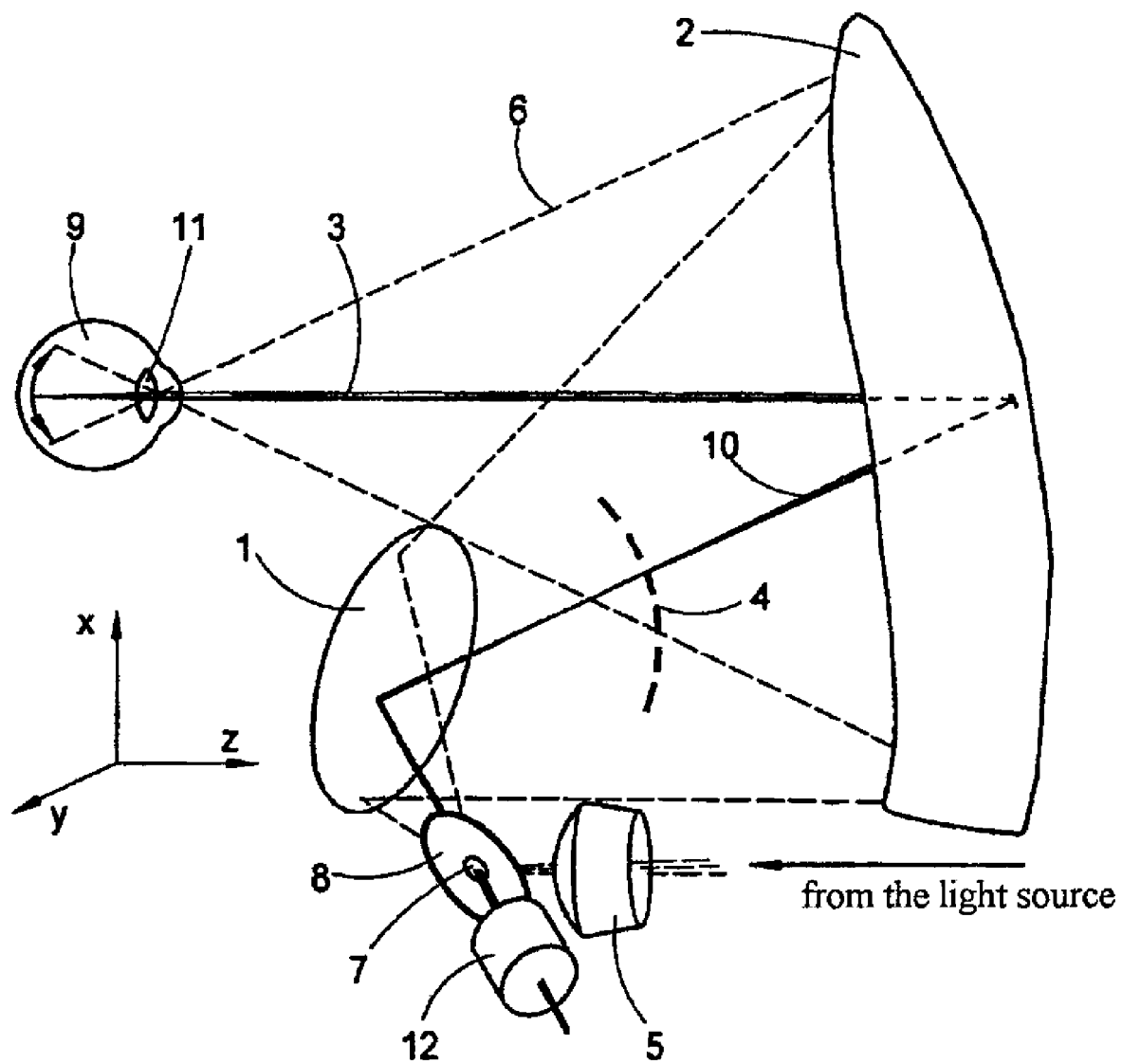
FIG. 1 shows an optical system with two freeform mirrors.

FIG. 1 is a highly schematic view of a possible advantageous embodiment example of an optical system for implementing reflection-free opthalmoscopy, particularly with a fundus camera. Only the optical elements comprising a substantially coaxial illumination beam path and imaging beam path or observation beam path and camera beam path are shown in a simplified manner without mounts or other mechanical holding devices.

A mirror system comprising two imaging, reflecting optical elements in the form of mirrors 1 and 2 is provided for implementing these beam paths. At least one of these two mirrors 1 or 2 is constructed as a freeform mirror with an imaging, reflecting freeform surface.

In the embodiment example according to FIG. 1, the mirrors 1 and 2 each have a freeform surface as imaging surface having the following constructional data:

a translation of the coordinate system with respect to the eye pupil (in air) of:

| Coordinate | X [mm] | Y [mm] | Z [mm] |
| --- | --- | --- | --- |
| Eye pupil | 0.0000000 | 0.0000000 | 0.0000000 |
| Mirror 1 | −6.8487090 | −165.4836370 | 47.0325630 |
| Mirror 2 | 293.0630880 | −0.6361000 | −155.3942110 |
| Image of the illumination ring | 40.6840860 | 107.9439940 | 84.9774900; | a rotation of the coordinate system with respect to the eye pupil (in air) of:

| Angle of rotation | α [°] | β [°] | γ [°] |
|---|---|---|---|
| Eye pupil | 0.0000000 | 0.0000000 | 0.0000000 |
| Mirror 1 | 76.0042720 | −1.9900470 | 0.0000000 |
| Mirror 2 | 170.9745940 | −64.6866110 | 0.0000000 |
| Image of the illumination ring | −51.2908710 | 39.1319540 | 30.6900040; | and
a surface shape for mirrors 1 and 2 with respect to the respective surface coordinate system, which surface shape is defined by the following equation:

$$z=(p_x x^2+p_y y^2)/[1+\sqrt{1-(1+k_y)p_x^2 x^2-(1+k_y)p_y^2 y^2}]+c_1 x+c_2 y+c_3 x^2+c_4 xy+c_5 y^2+c_6 x^3+c_7 x^2 y+c_8 xy^2+c_9 y^3+c_{10}x^4+c_{11}x^3 y+\ldots;$$

where a polynomial development with the development constants $c_{1-27}$ has the following values for mirror 1:

| | $K_x = 0.000000000E+00$ | $K_y = 0.000000000E+00$ | | |
|---|---|---|---|---|
| | $1/\rho_x = -215.000$ | $1/\rho_y = -219.000$ | | |
| $c_{1-4}$ | 0.00000000E+00 | 0.00000000E+00 | −.11000521E−03 | −.14259467E−03 |
| $c_{5-8}$ | 0.36710319E−04 | 0.30325236E−06 | 0.39598788E−06 | .72428906E−06 |
| $c_{9-12}$ | −.22614328E−06 | 0.56301184E−08 | 0.18564567E−08 | −.17641549E−08 |
| $c_{13-16}$ | 0.300856709E−08 | −.11779725E−08 | −.16133079E−10 | −.29826733E−10 |
| $c_{17-20}$ | −.10722833E−11 | 0.47271735E−12 | −.20450551E−10 | .55932153E−11 |
| $c_{21-24}$ | −.15323720E−13 | 0.14840899E−12 | −.48945914E−13 | 0.22616480E−13 |
| $c_{25-27}$ | 0.15323720E−13 | 0.12953501E−13 | −.87761187E−15; | | where a polynomial development with the development constants $c_{1-27}$ has the following values for mirror 2:

| | $K_x = 0.000000000E+00$ | $K_y = 0.000000000E+00$ | | |
|---|---|---|---|---|
| | $1/\rho_x = 0.000$ | $1/\rho_y = 137.000$ | | |
| $c_{1-4}$ | 0.00000000E+00 | 0.00000000E+00 | 0.43292571E−03 | −.14593775E−03 |
| $c_{5-8}$ | −.42509202E−02 | −.28647132E−07 | 0.45437799E−06 | −.11927701E−05 |
| $c_{9-12}$ | 0.22797954E−05 | 0.39691471E−09 | 0.48994174E−09 | 0.22211437E−08 |
| $c_{13-16}$ | −.12740305E−08 | −.92954442E−08 | −.29905067E−12 | −.27840314E−11 |
| $c_{17-20}$ | −.42513819E−13 | −.56277965E−11 | −.45816012E−10 | −.24706205E−09 |
| $c_{21-24}$ | −.55720016E−15 | 0.18029456E−14 | −.34158468E−14 | −.48883050E−14 |
| $c_{25-27}$ | 0.33724484E−13 | 0.51120041E−12 | −.27001064E−11; | | and
where $\rho_x$ and $\rho_y$ are curvatures in the origin of the respective surface coordinate systems, $K_x$ and $K_y$ are conical constants, and x; y; z are the coordinates of the surface points of the mirrors.

In this connection, ρ designates curvatures of the surfaces at coordinates x and y; $K_x$ designates the sagittal conical constants; $K_y$ designates the meridional conical constants; and z designates the sagitta of points on the surfaces of the mirrors 1 and 2. The coordinate origin is located at the eye pupil.

In this way, by appropriately dividing the refractive forces, minimal imaging errors occur. The freeform surfaces are formed as symmetry-free surfaces and they are not surfaces of revolution, e.g., such as a spherical or parabolic surface.

An additional deflection of the beam paths is achieved by means of a mirror arrangement of the type mentioned above. Accordingly, small deflection angles are realized at the mirror 2, and a sufficient free distance A between the eye and the mirror 2 can be achieved. The imaging fidelity over an illumination field of appreciably greater than 30° can be realized in that at least one mirror 1 or 2 or both mirrors 1 and 2 is/are constructed with a freeform surface. The imaging quality is advantageously influenced over the entire illumination field and observation field when both mirrors 1 and 2 have freeform surfaces. In this arrangement of the two mirrors 1 and 2, there are two areas in which, depending on the inclination of the mirrors 1 and 2 relative to the optical axis 3 of the beam path, local regions of the mirror surfaces are sharply imaged on the fundus image (intermediate image). In this case, this is carried out in the range from approximately −6.0 dpt to −5.0 dpt for mirror 2. In the range from about +8.0 dpt to +13 dpt, surface defects in mirror 1 are sharply imaged on the fundus image. For visual acuity deficiencies in which the intermediate image lies on one of the two mirrors 1 or 2, impurities on the mirror surfaces can cause scattering effects in imaging. Accordingly, in this embodiment example, an intermediate image 4 is positioned between the mirrors 1 and 2 in such a way that there is no imaging of the mirror surfaces on the image of the retina in a range from −5.0 dpt to +8.0 dpt in which most visual acuity deficiencies occur. In this way, impurities, dirt or manufacturing defects on the mirror surfaces are prevented from being imaged on the retina image. For visual acuity deficiencies outside the given diopter range in which the intermediate image 4 lies on one of the mirrors 1 or 2, impurities on the mirror surfaces can be corrected by digital image processing.

To prevent dust or other impurities from settling on the surfaces of the mirrors 1 and 2 as far as possible, the mirrors 1 and 2 are arranged, for example, in a housing in such a way that their reflecting surfaces do not face upward.

The optical system of a fundus camera according to FIG. 1 comprises an illumination path 5 with an illumination beam path 6 (shown in dashes in FIG. 1) and with the imaging mirrors 1 and 2. The light from a light source, not shown, is guided into the eye by a deflecting mirror 8 provided with an aperture 7 and by mirrors 1 and 2 for illuminating the fundus of an eye 9 to be examined. In an imaging beam path 10, a fundus image is imaged in an intermediate image plane as intermediate image 4 through the eye lens 11 and the mirror 2. This intermediate image 4 is then imaged through the mirror 1 through aperture 7 of the deflecting mirror 8 into a downstream observation path or recording path 12 onto the receiver of a camera, not shown, or in an image plane of observation optics for visual observation.

To prevent contamination of the reflecting surfaces of the two mirrors 1 and 2, it is advantageous to provide a cover plate, particularly on the patient's side, which is arranged and dimensioned in such a way that reflections occurring on it cannot enter the observation path or recording path 12 and chromatic aberrations are kept at a minimum. This cover plate can also have an asymmetrical surface shape.

The mirrors 1 and 2 can also be protected from contamination by a thin foil which is arranged at an inclination to the optical axis 3 to prevent interfering reflections.

Figure 2:
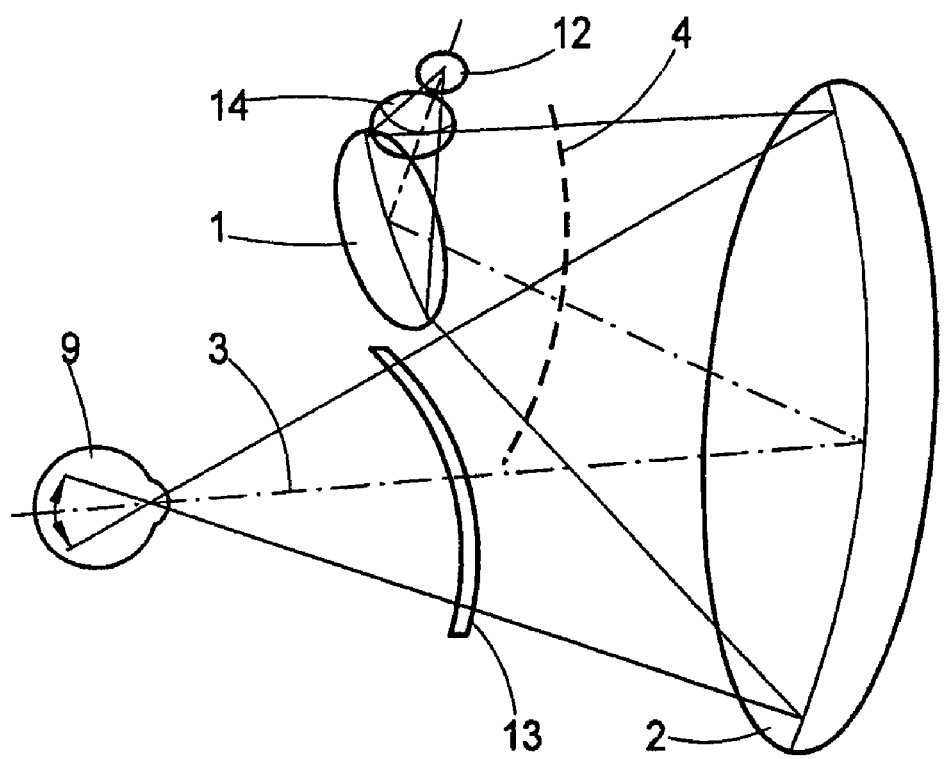
FIG. 2 shows an optical system with two freeform mirrors and cover plates for an encapsulated system.

For systems with particularly low scattered light, an encapsulated construction is advantageous. For example, FIG. 2 shows a highly simplified view of the elements of an encapsulated optical system with mirrors 1 and 2 and, advantageously, cover plates 13 and 14. In the embodiment example, cover plate 13 closes the surrounding housing on the patient's side and cover plate 14 closes the surrounding housing on the observation or recording side. In FIG. 2, the surrounding housing is omitted for the sake of simplicity. The two cover plates 13 and 14 are constructed and arranged in such a way that occurring reflections cannot enter the observation or recording path 12 and chromatic aberrations are sharply minimized. For improved correction of the imaging quality of the entire optical system comprising the cover plates 13 and 14 and mirrors 1 and 2, it can also be advantageous in this construction when the cover plates 13 and 14 have an asymmetrical surface shape.

Thin foils can also be provided in this case to prevent contamination of the mirrors 1 and 2 and can be arranged at an inclination to the optical axis 3 to prevent interfering reflections.

To simplify mounting and alignment of the two mirrors 1 and 2, it is advantageous to fix the two mirrors in a holder (not shown) after their alignment so that the position of the mirrors cannot change. Together with the holder, the mirrors 1 and 2 can be efficiently installed in the device in one mounting step without further alignment.

Figure 3:
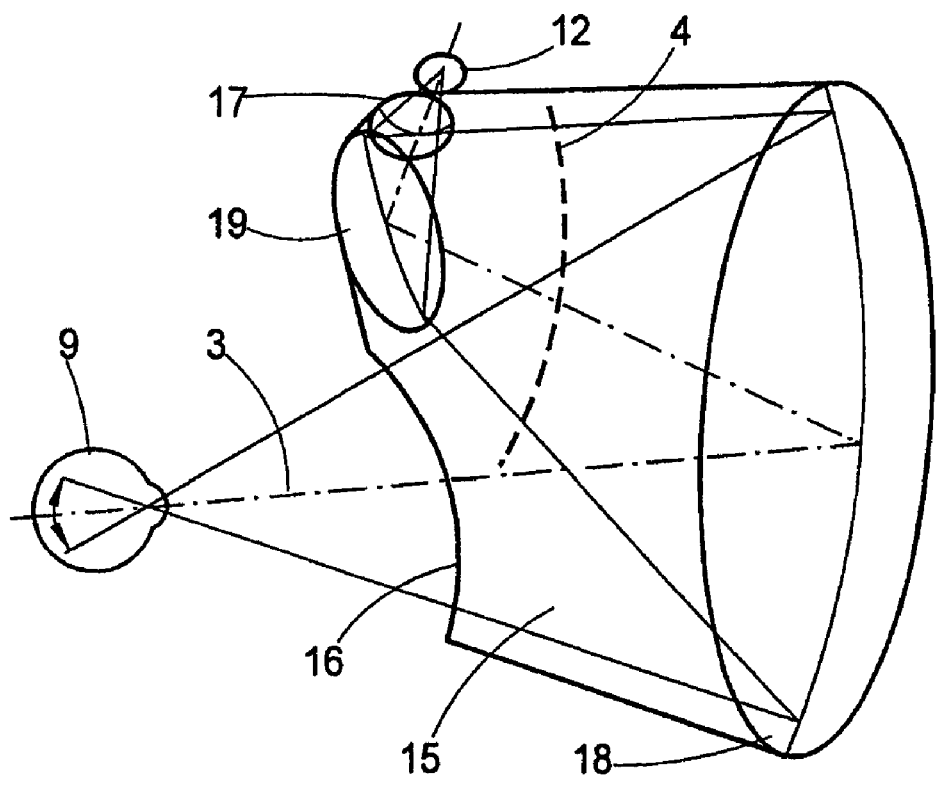
FIG. 3 shows a system of optical material with an index of refraction of n>1.

FIG. 3 shows a schematic view of another advantageous construction of the optical system according to the invention for reflection-free opthalmoscopy and for imaging the fundus. This system comprises a monolithic body 15 of optical material with a refractive index of n>1 at which the imaging reflective surfaces are arranged at precisely defined positions and with a precisely defined surface shape and has a light entry surface 16 and a light exit surface 17.

In this construction, the light path runs as follows: the entering light is refracted at the light entry surface 16, is then reflected at a first reflective surface 18 of the body 15, is then reflected at a second reflective surface 19 of the body 15, and the light then exits from the body 15 through the light exit surface 17 and is refracted at this surface.

As light-refracting surfaces, the light entry surface 16 and a light exit surface 17 must be designed and profiled in such a way that interfering reflections cannot enter the observation or recording path 12 and chromatic aberrations remain minimal. This can be achieved, for example, in that the light entry surface 16 and/or the light exit surface 17 have/has an asymmetrical or other suitable surface shape.

One advantage of the monolithic construction is that time-consuming alignment during production or possible realignment after extended use of the imaging mirrors relative to one another can be dispensed with. Further, this arrangement is very easy to assemble.

It has proven advantageous to design the fundus camera in such a way that the distance between the patient's eye and the mirror 2 next to the patient's eye is minimized. Accordingly, the dimensions of the optical system in its entirety can also be minimized. By minimizing this distance, there also results an advantageous shifting of the area in which local regions of the mirror surfaces are not sharply imaged on the fundus image and which is displaced in the direction of higher-order myopic vision deficiencies in such a way that more fundus images are made possible also in terms of percentage corresponding to the statistical frequency of visual acuity deficiencies without interference through surface defects on the mirrors 1 and 2.

An advantageous construction of the optical system according to the invention can also be designed in such a way that it is possible to influence the size and shape of the field and the size and shape of the pupil. This can be achieved in an advantageous manner with at least one electronically structurable or adaptive optical element in the optical system. For example, a structurable or adaptive element of this kind can be arranged in place of the deflecting mirror 8 (FIG. 1) or at another suitable location in the beam path of a fundus camera. By means of a structurable or adaptive element of this kind, asymmetries can be preserved, e.g., in the illumination beam path of a fundus camera, so that the requirements of the imaging system for reflection-free opthalmoscopy are reduced and production is simplified. The field size and pupil can be adapted to different application tasks in a simple manner through the use of elements of this kind.

Adaptive elements can also be used, for example, to compensate for device-specific errors or high-order visual acuity deficiencies so that an optimal correction of the fundus image is made possible and, for example, the physician is afforded advantages with respect to a diagnosis. In such cases, the adaptive element is advantageously arranged in the vicinity of the device pupil.

The optical system for reflection-free opthalmoscopy according to the invention has proven particularly advantageous when a fundus camera with this system is combined with laser applications for diagnosis and therapy.

The absence of chromatic aberrations is particularly advantageous in multicolor laser coagulation because the different wavelengths which are used have no deviations in the application plane. A registered, laser coagulation which is controlled in a spatially precise manner is facilitated by dispensing with veiling glare paths (reflections). The small quantity of optical components results in fewer optical interfaces and very short paths in optical media.

In optical coherence tomography (OCT) which uses light in the IR range, the absence of chromatic aberrations when combined with a fundus camera obviates additional corrections for the expanded spectrum. Unwanted interference by multiple reflections and scattered light does not occur.

The absence of chromatic aberrations in the system is particularly advantageous for therapy and diagnosis with ultrashort laser pulses, for example, in the femtosecond range, because additional corrections for shortening the pulse widths can be dispensed with.

In hyperspectral imaging and spectral imaging of the retina, the absence of chromatic aberrations in the system is advantageous in that additional elements for correcting the expanded spectral bandwidth can be dispensed with.

In fundus reflectometry, an artifact-free image is achieved by preventing veiling glare paths.

The optical system according to the invention can be applied in an advantageous manner in fundus cameras based on a traditional generation of color images parallel in time, with a new generation of color images sequentially with respect to time, or with a sequential multispectral fundus reflectometry with a monochrome chip.

Application of the freeform mirror optics in devices with OCT, confocal, or line laser scanners or in devices and/or methods for imaging the retina can also be advantageous.

Sharp, highly detailed, high-contrast images should be achieved for documenting medical findings concerning the eye. This is impeded by deficiencies (imaging errors) in the optical observation system and in the optical system of the eye when recording images from the interior of the eye (eye lens, vitreous humor, ocular fundus) and by voluntary and involuntary eye movements which ultimately lead to motion blurring and a deterioration of contrast. Deficiencies, e.g., imaging errors, in the optical observation system and optical system of the eye can be compensated by a suitable construction and design of the observation system by the method proposed herein. Eye movements lead to motion blur which nullifies all optical compensation if exposure times are too long during the recording of images. In order to suppress this motion blur, short exposures, advantageously in the millisecond range, must be carried out by means of a sufficiently high-power light source, for example, by means of a suitable flash lamp. This solution is used in the majority of known fundus cameras. For color recordings, the daylight-like spectrum of the flash lamp combined with a color-capable image sensor, e.g., with a surface sensor outfitted with color filters, is used. The disadvantage in this solution is that the spectral characteristic of these fixedly arranged color filters is not disclosed with sufficient accuracy and, above all, cannot be changed subsequently. Accordingly, there is only a limited possibility for optimal exposure control for the individual colors and color management that is adapted to the object.

In monochrome techniques, the desired spectral component from the white flash lamp is filtered out by color filters. This solution is not efficient in terms of energy. A better solution consists in using LEDs in continuous and pulsed mode. LEDs with different emission wavelengths, e.g., red, green and blue for color recordings, are used. One or more LEDs with suitable wavelengths are used in monochrome techniques. Sufficiently short exposure times can be achieved in that the LEDs are switched on and off virtually without delays. The spectral characteristics of the LEDs are known with sufficient exactitude and can be influenced in an energy-efficient manner by filters so that an optimal color management can be realized in a simpler manner. When recording color images, it is useful to carry out the image acquisition for red, green and blue sequentially, i.e., using a high-sensitivity black-and-white image recorder, and the respective partial color image is integrated successively by pulsed LEDs. An optimal control can be achieved for the partial color images through the choice of pulse lengths and pulse heights. With continuous illumination for purposes of adjusting to the object being examined, a useful spectral light mixture adapted to the object can be achieved through a suitable choice of intensities of the LEDs which are used.

Further, chromatic aberrations can be selectively influenced synchronous with the respective spectral light pulses by means of the sequential operation. For example, an optimal correction can be achieved by specific adjustments of an adaptive element during a corresponding color light pulse. A similar effect can be achieved by an optical element whose position in the beam path is deliberately changed, e.g., in the form of a shift lens. In this way, the optical design can be simplified with respect to chromatic corrections because not all corrective measures need be applied simultaneously.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMBERS

1; 2 mirror
3 optical axis
4 intermediate image
5 illumination path
6 illumination beam path
7 aperture
8 deflecting mirror
9 eye
10 imaging beam path
11 eye lens
12 observation path or recording path
13; 14 cover plate
15 monolithic body
16 light entry surface
17 light exit surface
18 reflective surface

The invention claimed is:

1. An optical system for reflection-free ophthalmoscopy having a beam path with reflective, or refractive and reflective, optical elements which are used substantially in common for illumination, observation, and/or recording, the optical system comprising:
   a plurality of reflecting optical elements, or a plurality of reflecting and refracting optical elements, for illuminating and imaging the fundus;
   wherein the plurality of reflecting, or reflecting and refracting, optical elements comprises a mirror system including at least two freeform mirror optical elements which are formed as freeform mirrors, each with an imaging, reflecting freeform surface;
   wherein the optical elements are arranged in a housing in a precisely defined position and attitude relative to one another in such a way that an imaging of reflecting surfaces of the optical elements on the image of the retina is prevented within a diopter range of the patient's eye to be examined; and
   wherein the freeform mirrors are formed as symmetry-free freeform mirrors between which an intermediate image plane is located.

2. The optical system according to claim 1;
   wherein the mirror system is arranged so as to be encapsulated in a housing which is closed by a first cover plate at the side facing the patient and a second cover plate at the side facing the observer;
   wherein the cover plates have a surface shape such that interfering reflections are prevented and chromatic aberrations are minimized.

3. The optical system according to claim 1;
   wherein the optical elements of the mirror system are arranged in the housing in a common holder or receptacle in a precisely defined position and attitude relative to one another.

4. An optical system for reflection-free ophthalmoscopy having a beam path with reflective, or refractive and reflective, optical elements which are used substantially in common for illumination, observation, and/or recording, the optical system comprising:
- a plurality of reflecting optical elements, or a plurality of reflecting and refracting optical elements, for illuminating and imaging the fundus;
- wherein the plurality of reflecting, or reflecting and refracting, optical elements comprises a mirror system including at least two freeform mirror optical surfaces which are formed as freeform mirrors, each with an imaging, reflecting freeform surface;
- wherein the optical elements are arranged in a housing in a precisely defined position and attitude relative to one another in such a way that an imaging of reflecting surfaces of the optical elements on the image of the retina is prevented within a diopter range of the patient's eye to be examined;
- wherein the freeform mirrors are formed as symmetry-free freeform mirrors between which an intermediate image plane is located; and
- wherein the mirror system comprises:
  - a monolithic body of optical material with an index of refraction of n>1, at which the imaging reflective surfaces are provided at precisely defined positions and with a precisely predetermined surface shape;
  - a light entry surface; and
  - a light' exit surface;
  - wherein the light entry surface and the light exit surface each have a surface shape such that interfering reflections are prevented and chromatic aberrations are minimized.

5. The optical system according to claim 4;
wherein the light entry surface and/or light exit surface of the monolithic body arc/is shaped asymmetrically.

6. The optical system according to claim 1;
wherein at least one of the optical elements of the mirror system is constructed as a spectral color splitter.

7. The optical system according to claim 1;
wherein at least one reflective, electronically structurable or adaptive optical element is provided in the beam path.

8. The optical system according to claim 1;
wherein the following coordinates for the position of mirrors (1) and (2) correspond to:
a translation of the coordinate system with respect to the eye pupil (in air) of:

| Coordinate | X [mm] | Y [mm] | Z [mm] |
|---|---|---|---|
| Eye pupil | 0.0000000 | 0.0000000 | 0.0000000 |
| Mirror 1 | −6.8487090 | −165.4836370 | 47.0325630 |
| Mirror 2 | 293.0630880 | −0.6361000 | −155.3942110 |
| Image of the illumination ring | 40.6840860 | 107.9439940 | 84.9774900; | a rotation of the coordinate system with respect to the eye pupil (in air) of:

| Angle of rotation | α [°] | β [°] | γ [°] |
|---|---|---|---|
| Eye pupil | 0.0000000 | 0.0000000 | 0.0000000 |
| Mirror 1 | 76.0042720 | −1.9900470 | 0.0000000 |
| Mirror 2 | 170.9745940 | −64.6866110 | 0.0000000 |
| Image of the illumination ring | −51.2908710 | 39.1319540 | 30.6900040; | and
a surface shape for mirrors 1 and 2 with respect to the respective surface coordinate system, which surface shape is defined by the following equation:

$$z=(p_x x^2+p_y y^2)/[1+\sqrt{1-(1+k_y)p_x^2 x^2-(1+k_y)p_y^2 y^2}]+c_1 x+c_2 y+c_3 x^2+c_4 xy+c_5 y^2+c_6 x^3+c_7 x^2 y+c_8 xy^2+c_9 y^3+c_{10} x^4+c_{11} x^3 y+\ldots;$$

where a first polynomial development with the development constants $c_{1-27}$ has the following values for mirror 1:

| | $K_x = 0.000000000E+00$ | $K_y = 0.000000000E+00$ | | |
|---|---|---|---|---|
| | $1/\rho_x = -215.000$ | $1/\rho_y = -219.000$ | | |
| $c_{1-4}$ | 0.00000000E+00 | 0.00000000E+00 | −.11000521E−03 | −.14259467E−03 |
| $c_{5-8}$ | 0.36710319E−04 | 0.30325236E−06 | 0.39598788E−06 | .72428906E−06 |
| $c_{9-12}$ | −.22614328E−06 | 0.56301184E−08 | 0.18564567E−08 | −.17641549E−08 |
| $c_{13-16}$ | 0.300856709E−08 | −.11779725E−08 | −.16133079E−10 | −.29826733E−10 |
| $c_{17-20}$ | −.10722833E−11 | 0.47271735E−12 | −.20450551E−10 | .55932153E−11 |
| $c_{21-24}$ | −.15323720E−13 | 0.14840899E−12 | −.48945914E−13 | 0.22616480E−13 |
| $c_{25-27}$ | 0.15323720E−13 | 0.12953501E−13 | −.87761187E−15; | | where a second polynomial development with the development constants $c_{1-27}$ has the following values for mirror 2:

| | $K_x = 0.000000000E+00$ | $K_y = 0.000000000E+00$ | | |
|---|---|---|---|---|
| | $1/\rho_x = 0.000$ | $1/\rho_y = 137.000$ | | |
| $c_{1-4}$ | 0.00000000E+00 | 0.00000000E+00 | 0.43292571E−03 | −.14593775E−03 |
| $c_{5-8}$ | −.42509202E−02 | −.28647132E−07 | 0.45437799E−06 | −.11927701E−05 |
| $c_{9-12}$ | 0.22797954E−05 | 0.39691471E−09 | 0.48994174E−09 | 0.22211437E−08 |
| $c_{13-16}$ | −.12740305E−08 | −.92954442E−08 | −.29905067E−12 | −.27840314E−11 |
| $c_{17-20}$ | −.42513819E−13 | −.56277965E−11 | −.45816012E−10 | −.24706205E−09 |
| $c_{21-24}$ | −.55720016E−15 | 0.18029456E−14 | −.34158468E−14 | −.48883050E−14 |
| $c_{25-27}$ | 0.33724484E−13 | 0.51120041E−12 | −.27001064E−11; | | and where $\rho_x$ and $\rho_y$ are curvatures in the origin of the respective surface coordinate systems, $K_x$ and $K_y$ are conical constants, and x; y; z are the coordinates of the surface points of the mirrors.

9. The optical system according to claim 1, further comprising:
   a means for generating sequential light pulses in different spectral regions;
   a means for synchronized image acquisition by means of an image sensor; and
   a means for image processing for displaying and storing at least one color or monochrome image.

10. The optical system according to claim 1, further comprising:
   one or more adjustable optical elements which change their position synchronously with light pulses for selective compensation of chromatic aberrations.

11. The optical system according to claim 1, further comprising:
   a means for selective compensation of chromatic aberrations by means of optical elements of at least one adaptive optical component which are adjusted synchronously with light pulses.

12. A device for laser coagulation comprising:
   the optical system according to claim 1.

13. A device for carrying out optical coherence tomography (OCT) comprising:
   the optical system according to claim 1.

14. A device for the diagnosis and therapy of the eye by ultrashort pulse lasers, comprising:
   the optical system according to claim 1.

15. The optical system according to claim 1;
   wherein it is used in hyperspectral imaging or in multispectral imaging for diagnosing retinal functions.

16. The optical system according to claim 1;
   wherein it is used in fundus reflectometry.

17. A fundus camera comprising:
   the optical system according to claim 1, which is used based on a generation of color images parallel in time or based on a new generation of color images sequentially in time, or based on a sequential multispectral fundus reflectometry with a monochrome chip or black-and-white chip.

18. The optical system according to claim 1;
   wherein the freeform mirror optics are used in devices with OCT, or in devices with point or line laser scanners, or in device and/or methods for imaging the retina.

19. A confocal laser scanner comprising:
   the optical system according to claim 1.

20. An opthalmological device comprising:
   the optical system according to claim 1;
   wherein LEDs operate in continuous operation and/or in pulsed operation as illumination source.

* * * * *